United States Patent [19]

Kee et al.

[11] Patent Number: 5,711,294
[45] Date of Patent: Jan. 27, 1998

[54] VENTILATOR MANIFOLD HAVING CLEANING PORTS AND METHOD OF USE THEREOF

[75] Inventors: Kok-Hiong Kee, St. Louis; Ari M. Bai, University City, both of Mo.

[73] Assignee: Sherwood Medical Company, St. Louis, Mo.

[21] Appl. No.: 360,499

[22] Filed: Dec. 21, 1994

[51] Int. Cl.⁶ ............................. A62B 9/04; A62B 7/10; A62B 19/00; A62B 23/02
[52] U.S. Cl. ............................. 128/202.27; 128/207.14; 128/205.12; 128/912; 604/326
[58] Field of Search ............ 128/200.24, 205.12, 128/202.27, 204.18, 912, 207.14; 604/267, 163, 171, 192, 263, 326

[56] References Cited

U.S. PATENT DOCUMENTS

| | | | |
|---|---|---|---|
| 3,991,762 | 11/1976 | Radford | 128/276 |
| 4,465,485 | 8/1984 | Kashmer et al. | 128/205.12 |
| 4,674,496 | 6/1987 | Svadjian et al. | 128/207.16 |
| 4,805,609 | 2/1989 | Roberts et al. | 128/200.21 |
| 4,850,350 | 7/1989 | Jackson | 128/207.16 |
| 4,852,563 | 8/1989 | Gross | 128/202.27 |
| 4,953,547 | 9/1990 | Poole, Jr. | 128/203.12 |
| 5,025,806 | 6/1991 | Palmer et al. | 128/203.12 |
| 5,060,646 | 10/1991 | Page | 128/207.14 |
| 5,062,420 | 11/1991 | Levine | 128/204.18 |
| 5,119,807 | 6/1992 | Roberts et al. | 128/200.21 |
| 5,228,436 | 7/1993 | Parkin | 128/205.12 |
| 5,388,571 | 2/1995 | Roberts et al. | 128/205.12 |
| 5,487,381 | 1/1996 | Jinotti | 128/207.14 |

*Primary Examiner*—Kimberly L. Asher
*Attorney, Agent, or Firm*—Ari M. Bai; Montgomery Smith

[57] ABSTRACT

A ventilator manifold provided with access ports and method thereof for accessing the interior chamber of the manifold and cleansing secretions from the inner wall of the manifold's interior chamber with a cleaning device without having to disconnect the patient from the respiratory support system.

18 Claims, 6 Drawing Sheets

VENTILATOR MANIFOLD HAVING CLEANING PORTS AND METHOD OF USE THEREOF

BACKGROUND OF THE INVENTION

1. Field of the Invention

This invention relates generally to apparatus used in conjunction with respiratory support systems. More specifically, the present invention relates to a ventilator manifold with ports that allow for direct access to the interior chamber thereof for cleaning.

2. Prior Art

Respiratory support systems used for the ventilation of critically ill patients are now commonly used in medical facilities. Typically, a prior art respiratory support system includes a tracheal tube, positioned either directly or through the nose or mouth into the trachea of a patient, and a ventilator manifold connected to the tracheal tube and to a source of breathable gas. The ventilator manifold also includes a port for "weaning" patients off the respiratory system and another port for attaching accessory devices thereto for specific purposes.

One example of an accessory device used in conjunction with the accessory access port of the manifold is a sheathed suction catheter. When a patient is attached to the respiratory support system, the suction catheter attached to the accessory access port is periodically used to aspirate the patient's lungs, however contaminants from the patient's secretion tend to coat both the catheter tube as well as the interior chamber of the manifold during use. As a result, the catheter must be cleaned after each use.

U.S. Pat. No. 3,991,762 to Radford is exemplary of the general prior art effort to solve this cleaning problem. The Radford device includes a small cleaning opening in its manifold accessory access port which allows cleaning liquid to be sprayed onto the tip of the withdrawn catheter, which is then suctioned into the catheter. The result is a rinsing of the secretions from the distal end of the catheter.

Nevertheless, Radford fails to address the problem of secretion accumulation in the interior chamber of the ventilator manifold. Instead of being cleaned by this process, Radford's interior chamber becomes increasingly coated with secretions that prevent necessary observation of the mucus by medical personnel. Further, this accumulation of secretions makes viewing of the ventilator manifold aesthetically distracting. The ventilator manifold must allow for clear viewing of its interior chamber so that the mucus from the patient's lungs may be examined by medical personnel as it is being expectorated by the patient in order to assist them in accessing the patient's condition. When the interior chamber becomes clogged with secretions over time, viewing the condition of mucus being expectorated by the patient becomes exceedingly difficult. Existing prior art procedures require disconnecting the patient from the respirator by first disconnecting the manifold from the patient's tracheal tube and leaving the patient off the ventilation system while the medical assistant cleans the inside of the manifold with a saline solution and then shakes the manifold dry of any remaining residue. However, interruption of the patient's ventilation in this manner is generally contraindicated due to the stress on the patient's respiratory system while off the respirator.

As of yet, nothing in the prior art has addressed the problem of properly and effectively cleansing the interior chamber of the manifold in order to extend the useful life thereof without a concurrent loss of ventilator assisted respiratory support to the patient. Specifically, there has been no design consideration for the attachment of a cleaning device to the manifold body that will effectively cleanse and evacuate secretions and other contaminants from the interior chamber of the manifold. Moreover, no procedural consideration has existed for properly cleaning the inside of the ventilator manifold without concurrent loss of respiratory support to the patient.

There therefore exists a need in the art for a ventilator manifold which is designed to allow direct access to its interior chamber for cleansing it of unsightly contaminants which accumulate during use.

BRIEF SUMMARY AND OBJECT OF THE INVENTION

In brief summary, the present invention overcomes and substantially alleviates the deficiencies in the prior art by providing access ports and method thereof for accessing the interior chamber of a ventilator manifold and cleansing secretions from the inner wall of the manifold's interior chamber with a cleaning device.

Accordingly, it is the principle object of the present invention to provide a reliable, medical, ventilator manifold in combination with a cleaning device for cleansing the inside of the ventilator manifold of secretions.

A further object of the present invention is to provide direct access to the interior chamber of a ventilator manifold by a cleaning device without interrupting the ventilation of the patient.

Another paramount object of the present invention is to provide a ventilator manifold that allows access without disturbing the possibly ongoing use of the manifold, the weaning port, accessory access port, or ventilation port of the manifold.

These and other objects of the present invention are realized in a presently preferred embodiment thereof, described by way of example and not necessarily by way of limitation, which provides for a ventilator manifold with cleaning ports in combination with a cleaning device for attachment to or insertion through, one or more of the cleaning ports for irrigating and evacuating secretions that have accumulated on the inner wall of the interior chamber of the manifold over time.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE ILLUSTRATED EMBODIMENT

Figure 1:
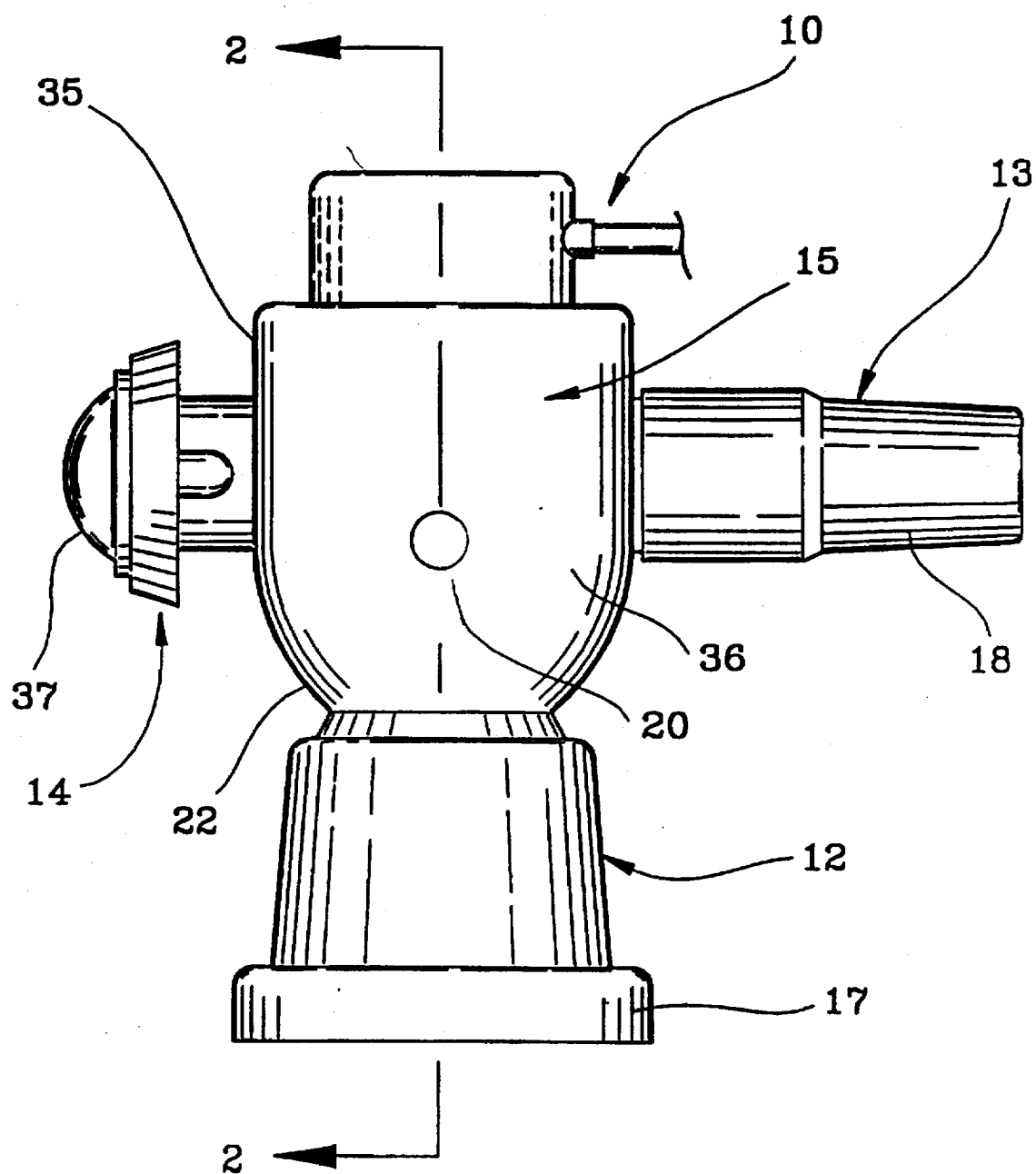
FIG. 1 is a perspective of the ventilator manifold of the present invention showing the preferred embodiment of two opposing ports.

As shown in the exemplary drawings for the purposes of illustration, a preferred embodiment of a ventilator manifold made in accordance with the principles of the present invention, referred to generally by reference numeral 10, is provided with at least one access port for use in combination with a cleaning device to facilitate direct access to the interior chamber of the manifold for cleaning.

As shown in FIG. 1, the ventilator manifold 10 of the present invention includes a plurality of ports which facilitate its connection to a patient and to a ventilator circuit of well known respiratory support system (not shown). The manifold 10 is attached to the patient for fluid flow communication with the patient's lungs by the connection of the tracheal attachment port 12 thereof to the connector of an endotracheal tube assembly (not shown) which has been previously positioned in the trachea of a patient by any one of several well known procedures.

The weaning port 14 is normally kept covered by a cap 37, and the ventilator circuit connection port 13 of the manifold 10 is connected to flexible breathing hoses from the respiratory support system in a well known manner, such as through a "Y" site connector.

The ventilator circuit connection port 13 and the patient attachment port 12 may, if desired, include swivel connectors 17 and 18 respectively thereon in order to allow relative rotation between the manifold 10 and the trachea tube to relieve the incidental forces caused by the manifold 10 or the breathing hoses attached thereto so as to increase the comfort of the patient.

The ventilator circuit attached to port 13 provides a high oxygen content gas mixture to the patient and receives the expelled air from the patient. The ventilator circuit commonly includes various valves, regulators and the like associated with the hoses attached to the port 13 to effect respiration of the patient. The manifold 10, and hoses attached thereto at port 13 are intended to be used by only one patient and then discarded.

The interior chamber 15 is made of a transparent material that allows medical personnel to view the inside of the chamber 15. The chamber 15 includes an upper section 35 and a lower section 36. The upper section 35 has a generally cylindrical interior surface while the lower section 36 of the interior chamber 15 forms a cylindrical lip portion 22 that extends upward from the patient attachment port 12 to the cleaning port 20 and functions to collect secretions that are coughed up by the patient that may drain down the inner surface of the chamber 15.

When attached to the patient, the entire respiratory system is designed to isolate the patient's lungs from the atmosphere and allow pressurized forced ventilation of a gas mixture of a high oxygen content from the ventilator into the patient's lungs. Commonly, respiratory support systems of this type are used to maintain a positive end expiratory pressure (PEEP) within the ventilator manifold 10 and the patient's lungs at all times during exhalation. This technique is used because of its benefit of ensuring that a minimum concentration of oxygen is supplied to the patient to maintain proper blood oxygenation levels. The PEEP procedure also keeps a large number of lung alveoli of the patient open at all times during respiratory support, thus increasing the effective lung area subject to ventilation.

Prevailing respiratory support techniques, including PEEP, have made it disadvantageous to interrupt respiratory support to the patient in order to either clean the catheter being used to aspirate the patient's lungs or cleanse the interior chamber 15 of the ventilator manifold 10 so that medical personnel may view the color and condition of mucus being expectorated by the patient inside the interior chamber 15. Catheters, under normal medical practice, must be disposed of after each use or the Radford method must be employed to clean the catheter after it has been withdrawn from the ventilator manifold 10 in order to extend the life of the catheter for even 24 hours. Prior art procedures to clean the interior chamber 15 of the manifold 10 have involved disconnecting the patient from the respiratory support system so that medical personnel could inject a saline solution into the interior chamber 15 and then shake dry the ventilator manifold 10 before reattaching the manifold 10. However, when this procedure takes an extended period of time to perform, the patient's blood oxygen levels can drop to inadequate levels, and cause the patient to over exert the lungs and heart when trying to return the blood oxygenation level to normal. Also, disconnecting the ventilator manifold 10 in order to cleanse the interior chamber 15 may expose the manifold 10 to contaminants.

The present invention resolves the problems associated with loss of isolation of the respiratory system from the atmosphere (i.e. loss of PEEP) when medical personnel must manually detach and cleanse the interior chamber 15 of the manifold 10. Specifically the ventilator manifold 10 of the present invention includes at least one cleaning port for inserting a cleaning device 19 (not shown) therethrough in order to cleanse the transparent surface of the interior chamber 15 without loss of PEEP.

Figure 2:
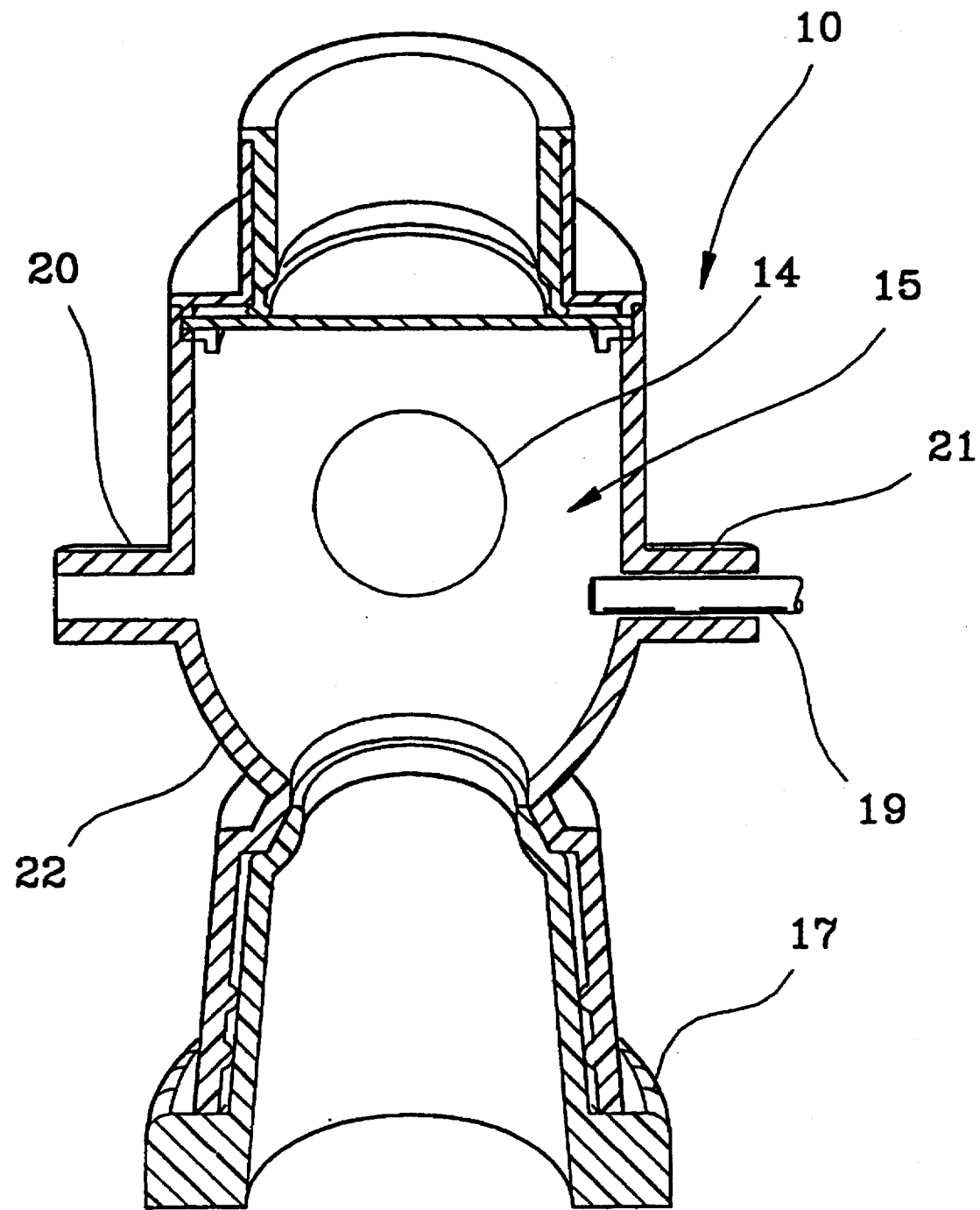
FIG. 2 is a cross-sectional view of the preferred embodiment of the invention taken along line 2—2 of FIG. 1.

As best shown in FIG. 2, the preferred embodiment of the present invention includes two opposing cleaning ports 20 and 21 which are positioned approximately in the same plane as the weaning port 14 and the ventilator circuit connection port 13 (not shown). The cleaning ports 20 and 21 are of a smaller diameter than the manifold ports in the prior art and are of a sufficient size to allow insertion or attachment of the cleaning device 19. Plugs (not shown) are used to cap the openings of the cleaning ports 20 and 21 in order to ensure air tight integrity of the ventilator manifold 10 during non-use and also prevent loss of PEEP in the respiratory support system. The cleaning device 19 can be a catheter, or the like, which has the capability of aspirating or irrigating the interior chamber 15 of secretions that coat the chamber 15 or to clean an aspirating catheter (not shown) that has been withdrawn from the patient's lungs through the tracheal tube (also not shown) but is still within the confines of the chamber 15. The configuration of opposing cleaning ports 20 and 21 also allows medical personnel to insert the cleaning device 19 into either port without having to disconnect the ventilator from the ventilator manifold be and to reorient the cleaning port 20 or 21 to an upward orientation that is accessible to medical personnel.

The preferred method of cleansing the interior chamber 15 of secretions which coat the surface of the chamber 15 and collect at the lip portion 22 is for medical personnel to uncap the plug to the cleaning port 20 or 21 and insert the cleaning device 19 into the chamber 15 therethrough. Medical personnel then perform an irrigating and aspiration operation, either consecutively or simultaneously, inside the chamber 15 using the cleaning device 19 until enough secretions are evacuated that allow clear viewing of the chamber 15. Finally, the cleaning device 19 is withdrawn from the interior chamber 15 and the cleaning port 20 is recapped with the plug.

Cleaning device 19 can also take the form of a tube which attaches over either cleaning port 20 or 21 as opposed to passing the device 19 through the cleaning port 20 or 21 and into the interior chamber 19 before cleansing the manifold 10.

Alternatively, another method of cleaning the ventilator manifold 10 can be accomplished, in part, by swiveling the manifold 10 using swivel connector 17 of the patient attachment port 12 so that one of the cleaning ports 20 or 21 is facing downward. The medical user then allows gravity to force the secretions coating the manifold 10 to flow downward until they accumulate near the opening of the cleaning port 20 or 21 on the interior surface of the interior chamber 15. Once sufficient accumulation has occurred, the medical user may uncap the cleaning port 20 or 21 and allow the secretions to flow out of interior chamber 15, thereby evacuating some of the secretions from the chamber 15 without use of cleaning device 19.

Figure 5:
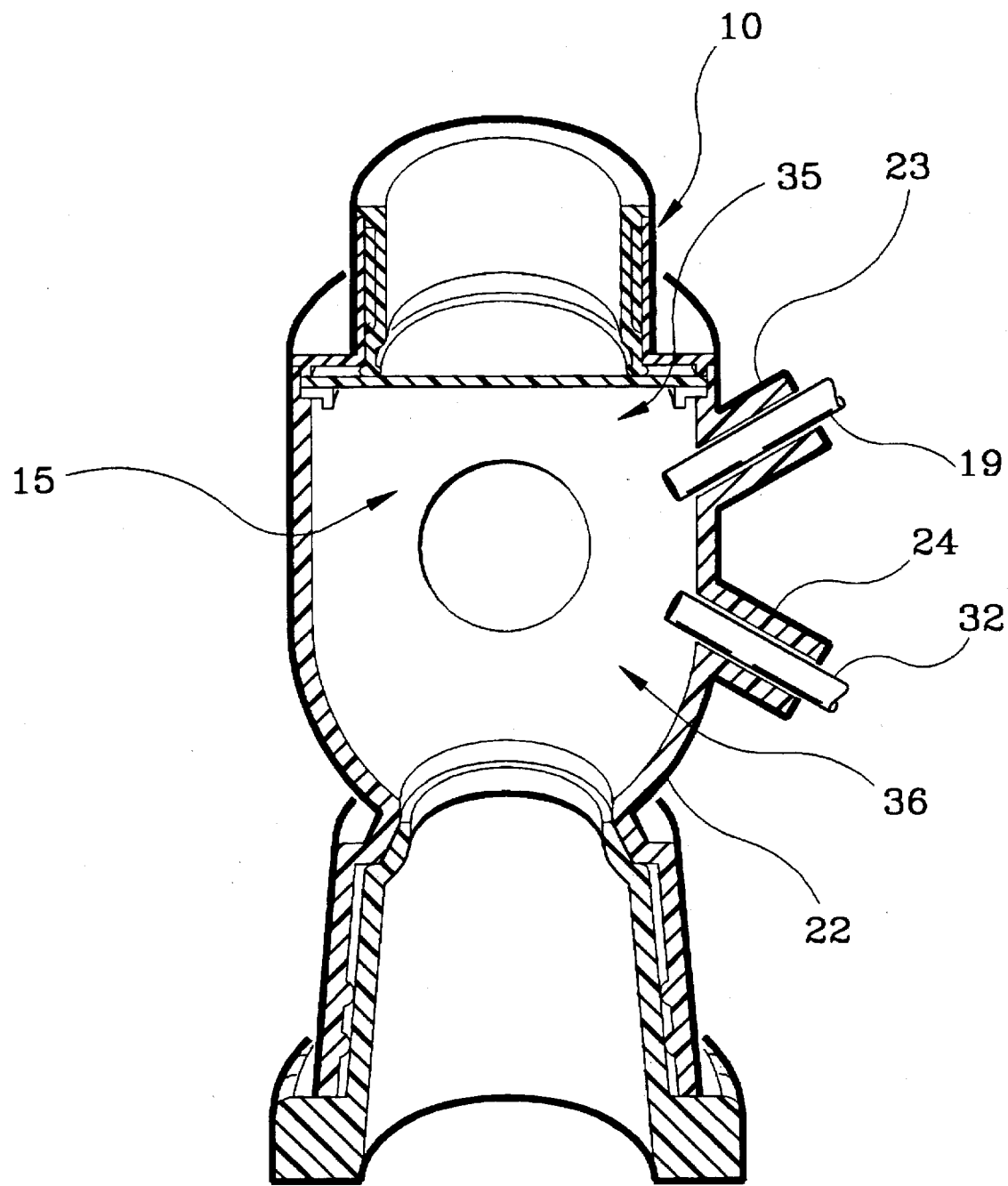
FIG. 5 is a perspective of the ventilator manifold showing another alternative embodiment of the present invention which includes two angled ports.

FIG. 5 shows an alternative embodiment to the ventilator manifold 10 that includes dual angled cleaning ports 23 and 24. The angled cleaning port 23 is located in the upper section 35 of the interior chamber 15 while the other angled cleaning port 24 is positioned above the lip portion 22 in the lower section 36 of the chamber 15. The cleaning ports 23 and 24 are slightly offset from one another in order to prevent cleaning devices 19 and 32 from crossing each other within the chamber 15 and thereby interfere with each other when operating simultaneously. Moreover, cleaning ports 23 and 24 are angled in such a manner that the extremities of either the upper section 35 or lower section 36 of the interior chamber 15 may be reached by cleaning device 19 through either angled cleaning port 23 or 24.

The angled cleaning ports 23 and 24 function in the same manner as cleaning port 20 of the preferred embodiment, except the angled cleaning ports 23 and 24 allow medical personnel to insert the cleaning device 19 into the interior chamber 15 at an angle without having to manipulate the device 19 after insertion. Thus, the angled configuration permits direct access to portions of the chamber 15 by the device 19 that the straight configuration of preferred embodiment does not allow. For example, the angled cleaning port 23 of the alternative embodiment permits direct access to the lip portion 22 of the chamber 15 by the cleaning device 19, thus allowing direct evacuation of secretions that have accumulated on the lip portion 22 without excessive manipulation of the device 19.

Figure 3:
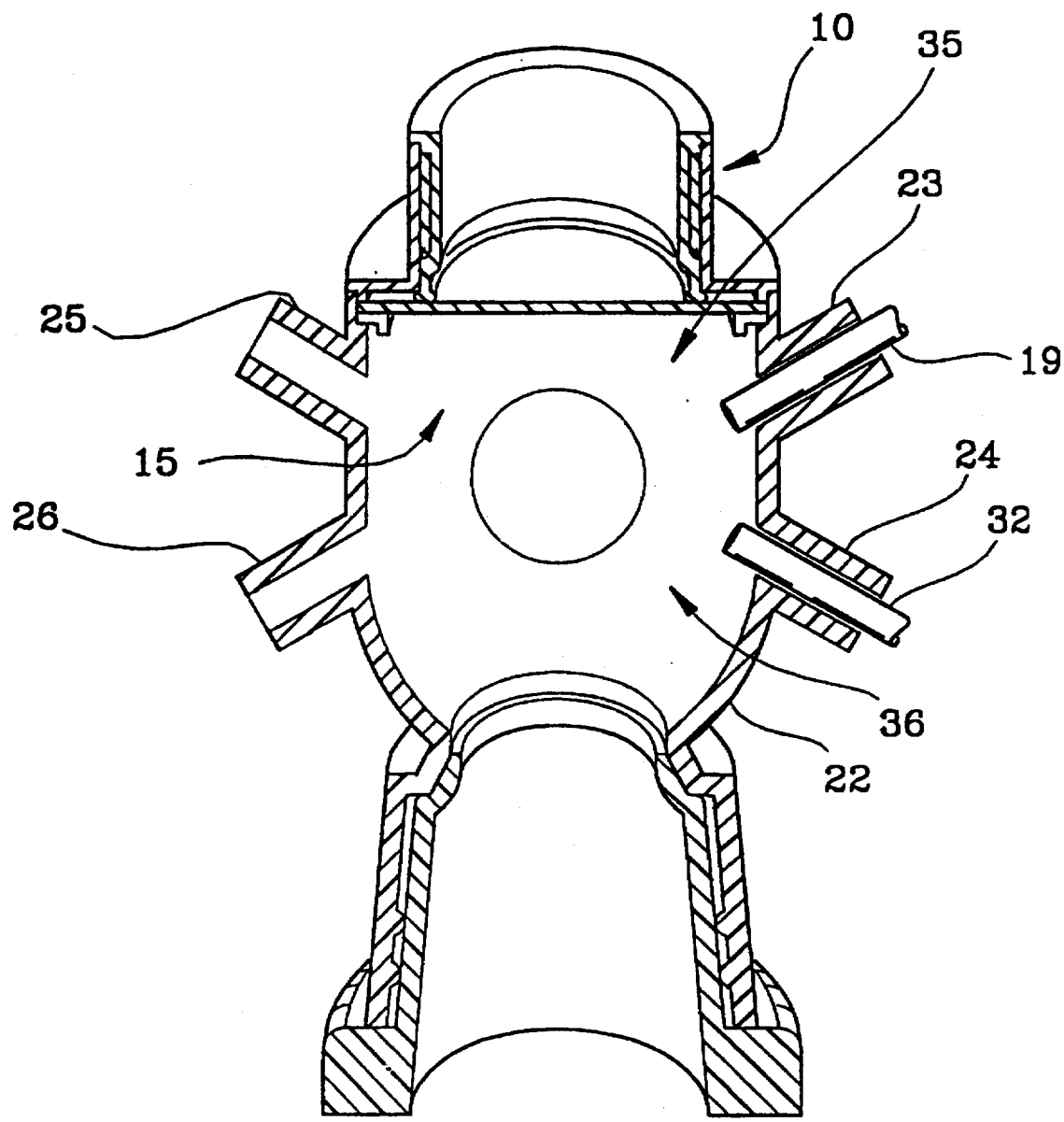
FIG. 3 is a perspective of the ventilator manifold showing an alternative embodiment of the invention which includes two dual opposing ports set at an angle to one another.

The dual configuration of the angled cleaning ports 23 and 24 may also permit the use of two cleaning devices 19 and 32 to simultaneously irrigate and aspirate the interior chamber 15 through separate cleaning ports 23 and 24. For ergonomic reasons previously detailed in the preferred embodiment, the ventilator manifold 10 can also include angled cleaning ports 25 and 26 on the opposing side of the manifold 10 if desired as illustrated in FIG. 3, so as to allow either side of the manifold 10 to be used without having to disconnect and reorient the manifold 10 in the correct direction.

The preferred method of use of the alternative embodiment involves uncapping the cleaning ports 23 and 24 and inserting the cleaning device 19 therethrough. Once the cleaning devices 19 and 32 are inserted in the interior chamber 15, the device 19 irrigates the upper section 35 of the chamber 15 while the device 32 aspirates secretions which have accumulated on the lip portion 22 including those secretions which flow downward to the lower section 36 as a result of the irrigating operation by device 19. Once the cleansing operation has sufficiently cleaned the interior surface of the interior chamber 15, the cleaning devices 19 and 32 are withdrawn from the interior chamber 15 and the cleaning ports 23 and 24 are recapped.

Figure 4:
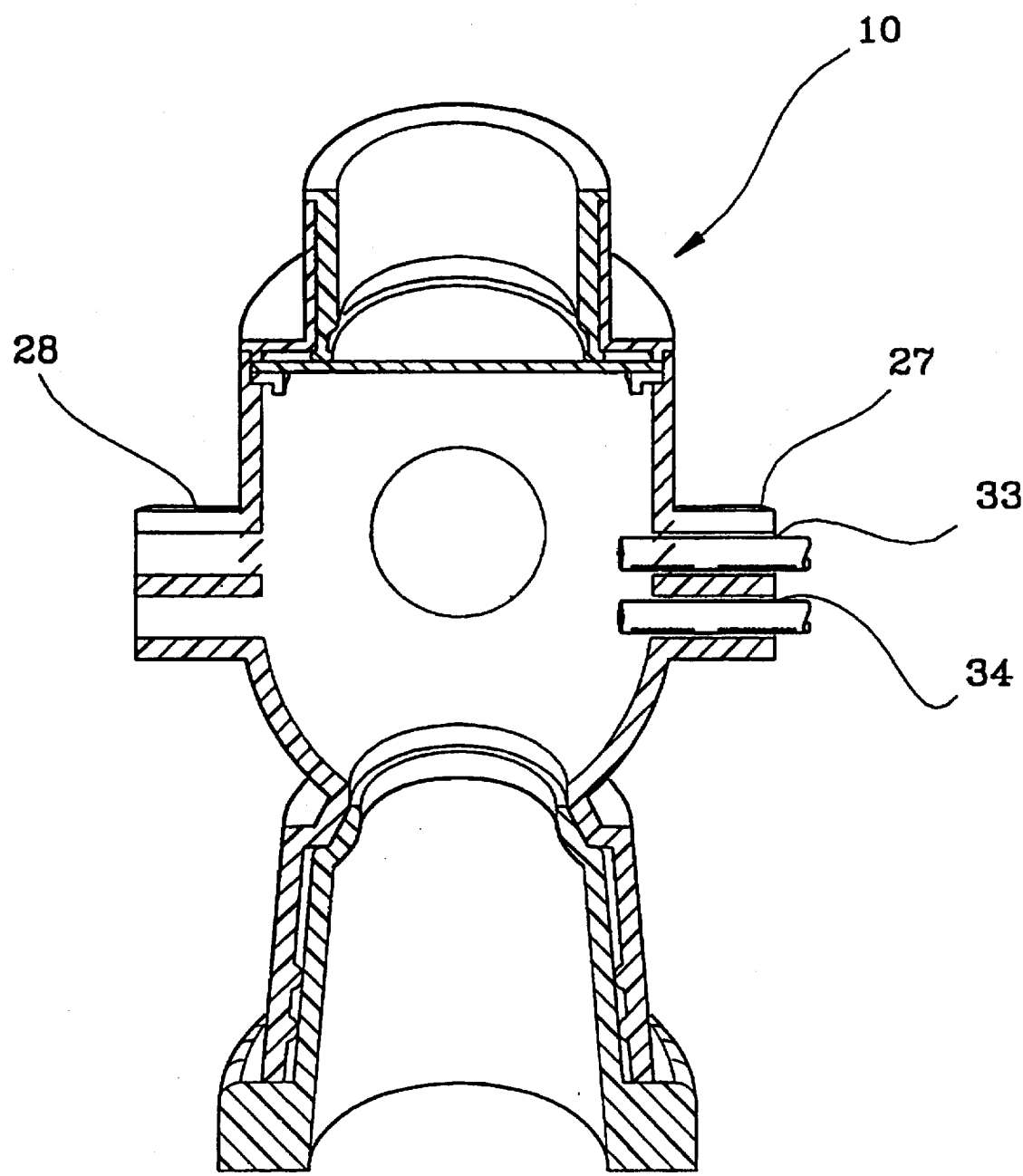
FIG. 4 is a perspective of the ventilator manifold showing another alternative embodiment of the present invention which includes two opposing ports having dual lumens.
Figure 6:
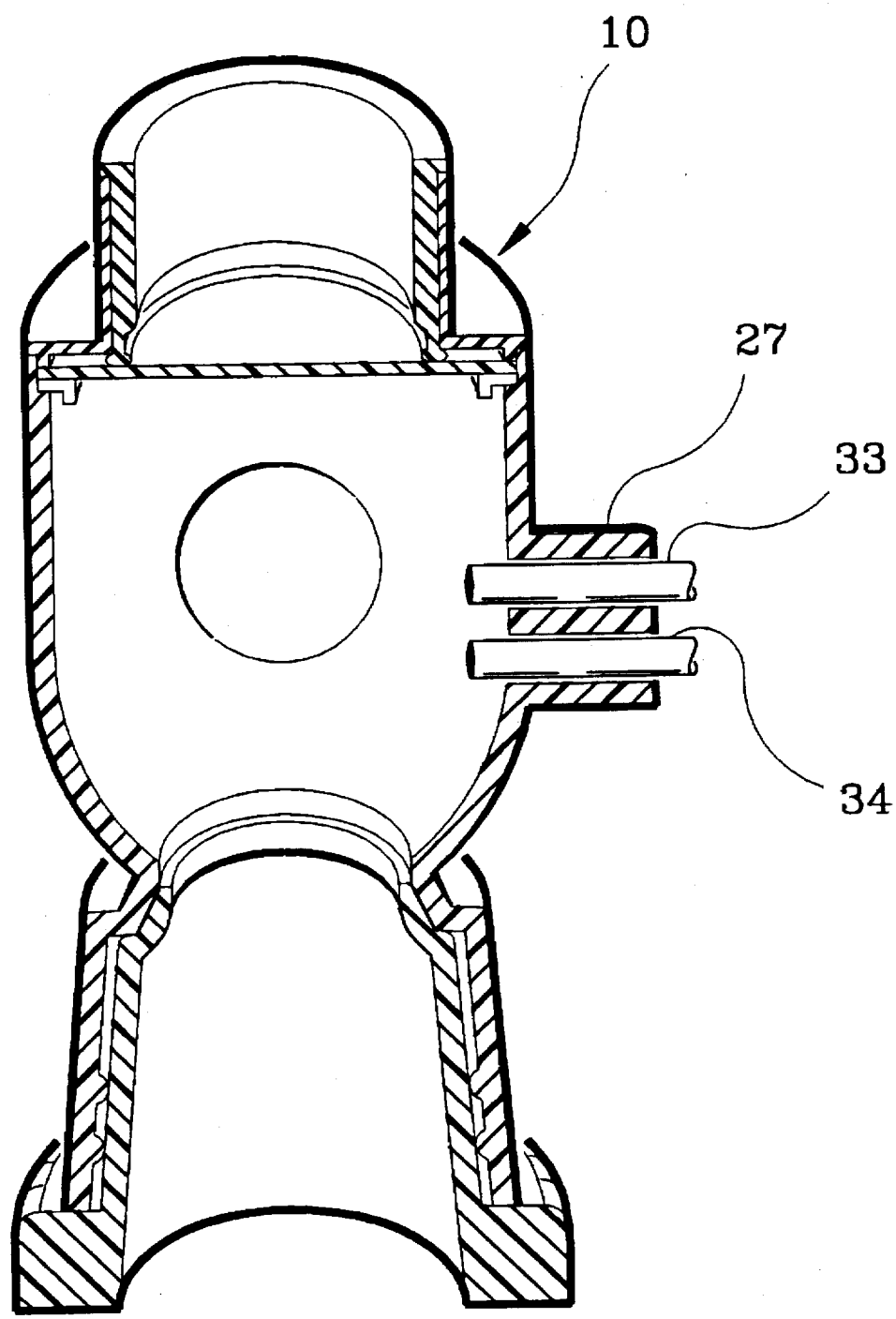
FIG. 6 is a perspective of the ventilator manifold showing another alternative embodiment of the present invention which includes a dual port.

Another alternative embodiment of the present invention is shown in FIG. 6, wherein the ventilator manifold 10 includes a cleaning port 27 with a straight line configuration having dual lumens 33 and 34. The dual lumen cleaning port 27 allows for simultaneous irrigation and aspiration of the interior chamber 15 through the same port by two different cleaning devices. As in the other embodiments, cleaning port 27 may also have an identical port 28 on the opposite side of the manifold 10 for ergonomic reasons as illustrated in FIG. 4.

Although particular embodiments of the invention have been shown, it is not intended that the invention be limited thereby, instead the scope of the present invention is intended to be limited only by the appended claims.

We claim:

1. A manifold having an interior chamber and a plurality of ports, including a first port for attachment to a tracheal tube and a second port for connection to a breathable gas source, means for cleaning said interior chamber of said manifold when in use for delivering PEEP to a patient and for maintaining positive end expiratory pressure while cleaning said interior chamber, said means for cleaning comprising at least one additional port sized for directly accessing and cleaning said interior chamber of said manifold with a cleaning device while said manifold is in use and connected to a patient.

2. The manifold according to claim 1, wherein said at least one additional port comprises at least two ports directly accessing said interior chamber of said manifold, said at least two ports being positioned at diametrically opposed locations around said interior chamber.

3. The manifold according to claim 2, wherein said at least two ports are smaller in diameter than anyone of said plurality of ports.

4. The manifold according to claim 2, wherein said at least two ports and said second port lie in a single plane.

5. The manifold according to claim 2, including at least two ports directly accessing said interior chamber of said manifold, said at least two ports being in angles position in relation to a manifold body.

6. The manifold according to claim 5, wherein said at least two ports are positioned directly above one another around said interior chamber.

7. The manifold according to claim 6, including two pairs of said at least two ports, said pairs being positioned at diametrically opposed locations around said interior chamber.

8. The manifold according to claim 2, including at least two ports directly accessing said interior chamber of said manifold, each of said at least two ports having dual lumens for access by two separate cleaning devices.

9. The manifold according to claim 8, said at least two ports being positioned at diametrically opposed locations around said interior chamber.

10. The manifold according to claim 8, wherein said at least two ports are smaller in diameter than anyone of said plurality of ports.

11. The manifold according to claim 8, wherein said at least two ports and said second port lie in a single plane.

12. A method of cleaning a manifold having an interior chamber and a plurality of ports, including a first port for attachment to a tracheal tube, a second port for connection to a breathable gas source, a third port for attachment of accessory devices thereto, a fourth port for weaning a patient off the respiratory support system, and at least one additional port sized for directly accessing and cleaning the interior chamber with at least one cleaning device while maintaining Positive End Expiratory Pressure, the method comprising the steps of:

a) connecting said manifold to a tracheal tube which is intubating a patient and a breathing gas source;

b) ventilating the patient with PEEP;

c) uncapping the at least one additional port while PEEP is being delivered to the patient;

d) cleaning the interior chamber with the at least one cleaning device; and e) recapping the at least one additional port after completion of said cleaning step the method being performed without disturbing patient ventilation.

13. The method of cleaning a manifold according to claim 12, wherein said step of cleaning further includes irrigating the interior chamber before suctioning out the interior chamber of secretions.

14. The method of cleaning a manifold according to claim 12, wherein the manifold includes at least two additional ports positioned at diametrically opposed locations around the interior chamber, and said step of inserting further includes inserting at least two cleaning devices into the at least two additional ports.

15. The method of cleaning a manifold according to claim 12, wherein the method of cleaning a manifold further includes inserting at least one cleaning device through the at least one additional port.

16. The method of cleaning a manifold according to claim 15, wherein said step of inserting the at least one cleaning device into the at least one additional port further includes introducing a saline solution into the interior chamber through the at least one cleaning device.

17. The method of cleaning a manifold according to claim 12, wherein said step of cleaning further includes attaching the at least one cleaning device to the at least one additional port.

18. The method of cleaning a manifold according to claim 12, wherein the said step of cleaning further includes swiveling one of the at least one additional port to a downward position and gravity draining the interior chamber of fluids through the at least one additional port.

\* \* \* \* \*